United States Patent

Larkin

[11] Patent Number: 5,279,571
[45] Date of Patent: Jan. 18, 1994

[54] ACCESS SITE FOR FLUID DELIVERY SYSTEM

[75] Inventor: Mark E. Larkin, Lindenhurst, Ill.

[73] Assignee: Abbott Laboratories, Abbott Park, Ill.

[21] Appl. No.: 25,904

[22] Filed: Mar. 3, 1993

Related U.S. Application Data

[63] Continuation of Ser. No. 816,019, Dec. 30, 1991, abandoned.

[51] Int. Cl.⁵ ............................................. A61M 5/00
[52] U.S. Cl. ................................... 604/167; 604/256
[58] Field of Search ................ 604/167, 256, 164, 169

[56] References Cited

U.S. PATENT DOCUMENTS

| | | | |
|---|---|---|---|
| 4,655,752 | 4/1987 | Honkanen et al. | 604/167 |
| 4,909,798 | 3/1990 | Fleischhacker et al. | 604/167 |
| 4,932,633 | 6/1990 | Johnson et al. | 604/256 |
| 4,935,010 | 6/1990 | Cox et al. | 604/167 |
| 5,078,689 | 1/1992 | Keller | 604/167 |
| 5,080,654 | 1/1992 | Picha et al. | 604/256 |

*Primary Examiner*—Paul J. Hirsch
*Attorney, Agent, or Firm*—A. Nicholas Trausch

[57] ABSTRACT

An access site for a fluid delivery system is disclosed. The apparatus comprises a rigid, tubular housing having a stepped inlet end, an outlet end and a bore therebetween, the stepped inlet end having an initial larger diameter cavity than the bore. Within the inlet end is a solid resilient sealing member having a larger and smaller cross dimensional portion positioned within the corresponding portions of the cavity and bore. The resilient member includes an axially parallel perforation and at least one axially protruding sealing ring on the large cross dimensioned portion of the sealing member in contact with a shoulder of the housing. Also included is a means for securing the member in the housing such that the resilient member experiences axial compressive forces at all points of axial contact between the member and housing.

6 Claims, 1 Drawing Sheet

ACCESS SITE FOR FLUID DELIVERY SYSTEM

This application is a continuation of application Ser. No. 07/816,019 filed Dec. 30, 1991 now abandoned.

BACKGROUND OF THE INVENTION

The present invention relates to an access site for a parenteral fluid delivery system and, more particularly, relates to an access site having a resilient, resealing member positioned in a housing cavity having parallel sidewalls and subjected to only axial compressive forces. Furthermore, the invention is directed to an access site of the type described herein including an axial perforation through the resilient resealing member which is especially useful with a blunt injection or connection device.

In general, parenteral fluids are often administered to patients from a syringe or other fluid container by a needle connection to a resealable access site of an I.V. administration set. A primary concern of the patient is that external contaminants don't enter the I.V. line through the injection site after the needle is removed. The access site must be guaranteed to reseal.

An equal anxiety among health care providers is that they are not exposed to infectious diseases, such as AIDS and hepatitis-B by accidental needle stick injuries. This concern by health care providers has led to an effort to reduce the number of sharp needles in the hospital environment. Central to this effort is the need to provide a reliable and resealable access site for parenteral fluids administered or connected by devices other than sharp needles. However, the access site must be versatile, since sharp needles will not be totally eliminated.

There are many known self-sealing injection sites usable with sharp needles. U.S. Pat. No. 4,416,661 titled "Injection Sites for Fluids" discloses one elastomeric plug held in a compression fit to resealably close a fluid entry port.

There are also known injection sites that are usable with blunt injection devices. For example, U.S. Pat. No. 4,197,848 discloses an injection site having a relatively thin molded sealing member that has an opening therethrough. A blunt injection device can be forced through the sealing member to place the injection device into fluid flow communication with the fluid flow path. Injection sites of this type use blunt injection devices and reduce the risk of needle stick for the health care provider.

It is important that the parenteral injection site reseal with enough force that viral or bacterial contaminants do not enter the parenteral flow path and infect the patient. Furthermore, it is desireable that parenteral fluids do not leak from the parenteral administration system.

A recent effort to provide a pre-slit injection site which can be used with a variety of solutions and over a range of fluid pressures is disclosed in published PCT Application No. PCT/US89/00273 (WO 89/06553) titled "Pre-Slit Injection Site and Tapered Cannula". This injection site incorporates a housing having an annular, tapered interior surface with the diameter of the tapered surface decreasing with increasing distance away from the housing opening. A cylindrical sealing member is positioned in the tapered interior surface so as to generate resealing radial forces increasing in value from an axial position adjacent the exterior peripheral surface of the injection site to a greater value interior from the peripheral surface. FIG. 27 of the application also discloses an alternate, non-tapered embodiment which is described as providing "compression to create a seal against pressure and a void region to accommodate deformed portions of the sealing member material only when the material is deformed or displaced by a blunt cannula piercing member."

All of the above described injection sites are deficient in providing at least one or more of a balance of reliable sealing around an inserted cannula as well as resealing after the cannula is removed, straightforward assembly and manufacture (without the need for void areas for example), ease of use with both sharp or blunt injection devices, reasonable active use life, sufficient engaging force to prevent inadvertent withdrawal of the cannula, and a minimal tendency to kickback the injection device out of the reseal member.

The present invention is directed to an alternative access site which is believed to provide advantages over the previously described unslit and pre-slit injection sites.

SUMMARY OF THE INVENTION

The access site of the present invention includes a rigid tubular housing having an inlet, an outlet and a bore therebetween. A cavity having parallel sidewalls with an internal cross dimension greater than the diameter of the bore is located at the inlet end of the housing. A resilient, self-sealing member is positioned in the inlet of the housing with a non-interference fit, i.e. that is without any radial compression of the resilient member. The resilient sealing member has a first small cross dimensioned portion positioned in the bore and a large cross dimensioned portion positioned in the inlet cavity. A securing member such as an annular cap member is fixed to the housing to secure the resilient sealing member in the housing and axially compress the resilient sealing member along axial points of contact between the resilient sealing member and the housing. Since there are only axial compressive forces and no radial compressive force gradient acting on the resilient member, the present invention tends to reduce an undesirable phenomenon referred to as kickback. Kickback is the situation when an injection device is inserted into the resilient sealing member but is gradually push out of the resilient sealing member by the unbalanced radial compressive forces.

In the preferred embodiments of the invention, the cross dimensions are circular. A cylindrical cavity is located at the inlet opening and a slightly smaller disk-shaped resilient sealing member is positioned therein. A cap member is fixed to the housing to produce only axial compressive forces that are equal at all points of contact and provide uniform annular sealing. The lack of unbalanced compressive forces allows an inserted injection device to remain in position rather than kickback the injection device as previously described.

According to a further embodiment, the present invention includes an axial perforation through the resilient sealing member. The perforation is normally closed by the inherent resiliency of the resilient sealing member. However, a blunt injection device can be readily inserted and retained in the pre-pierced access site, since kickback tendency is reduced due to the balanced axial distribution of the compressive forces.

According to a further configuration of the present invention, the resilient sealing member has at least one axially protruding annular sealing ring extending from the large cross dimensioned portion. This annular ring is axially compressed by the securing member (i.e. the annular cap member) which is fixed to the housing to produce the proper amount of axial compression on the resilient sealing member. In the preferred embodiment, there are two axially opposed sealing rings extending from opposite sides of the large cross dimensioned portion.

In the preferred embodiment the securing member is a cylindrical cap member having a center orifice of the same diameter as the bore of the housing. The orifice fits over the outward extending one of the small cross dimensioned portions of the resilient sealing member. The cap is fixed to the housing so as to axially compress the sealing rings against the housing and the cap member.

Numerous other advantages and features of the present invention will become readily apparent from the following detailed description of the invention, from the claims, and from the accompanying drawings.

DETAILED DESCRIPTION OF THE PREFERRED EMBODIMENT

Since this invention is susceptible of embodiments in many different forms, this specification and the accompanying drawings disclose multiple embodiments as examples of the invention. The invention is not intended to be limited to the embodiments so described, however. The scope of the invention is pointed out in the appended claims.

Figure 2:
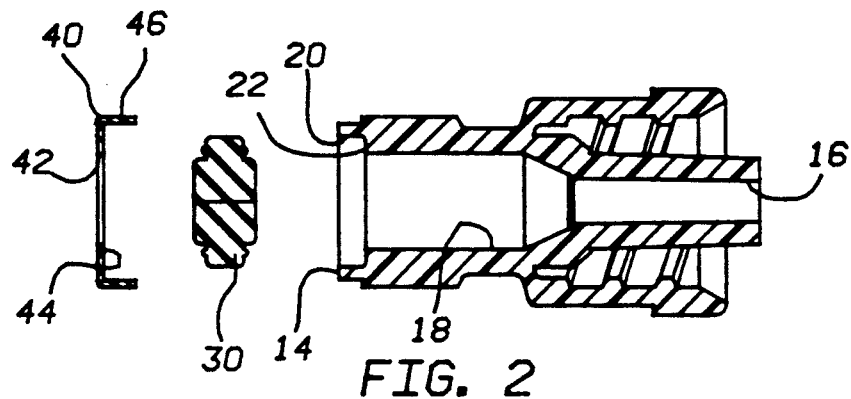
FIG. 2 illustrates an exploded view of the access site of FIG. 1.
Figure 1:
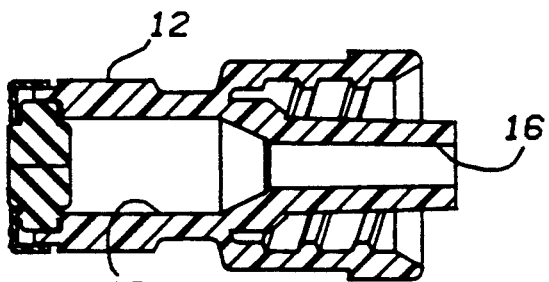
FIG. 1 is a side sectional view of an access site according to one embodiment of the present invention.

Turning now to FIG. 1 and FIG. 2, there is illustrated a first embodiment of an access site for a fluid delivery system. Specifically a new and novel male adapter injection site for a parenteral fluid administration set is disclosed. The adapter includes a rigid tubular housing 12 having an axial inlet 14 and axial outlet 16 and an axial bore 18 therebetween. An open cavity 20 at the inlet end of the housing has axially parallel sidewalls. The sidewalls do not taper and have a consistent internal cross dimension greater than the diameter of the bore 18. Preferably, the cavity 20 is cylindrical in shape, but it may be oval, square, hexagonal, etc. The larger cross dimension of the cavity 20 creates a seating shoulder 22 at the juncture of the cavity 20 and the bore 18.

Figure 3:
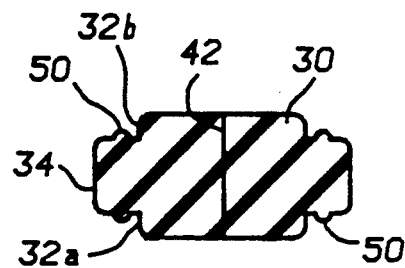
FIG. 3 illustrates an enlarged sectional of the resilient sealing member of FIG. 1 and FIG. 2.

A resilient sealing member 30 is positioned in the inlet cavity 20 with a non-interference fit. As best seen in FIG. 2 and FIG. 3, the resilient sealing member 30 has a large cross dimensioned portion 34 that has a cross dimension that is slightly less than the cross dimension of the cavity 20 but greater than the cross dimension of the bore 18. The large cross dimensioned portion 34 abuts the seating shoulder 22.

Resilient sealing member 30 is secured in the housing by a cap member 40 having a center orifice 42 which allows access to the resilient sealing member 30. Radial seating surface 44 surrounds the orifice. Axial flange 46 of the cap member 40 is secured to the housing 12 so as to provide axial compression to the axial points of contact between the resilient sealing member and the housing.

In a preferred embodiment, the resilient sealing member has two small cross dimension portions 32a and 32b axially extending from opposite ends of the large diameter portion 34. The cap member 40 has an orifice 42 sized to allow one of the small dimensioned portions 32a or 32b to axially project outside the cap member.

Further, at least one axially extending annular sealing ring 50a projects from one end of the large cross dimensioned portion 34 of the resilient sealing member. Preferably a second annular sealing ring 50b projects axially opposite from the opposite end of the large cross dimensioned portion.

The radial seating surface 44 of the cap member 40 secures the large dimensioned portion 34 of the resilient sealing member 30. The cap member 40 is fixed to the housing 12 so as to axially compress all points of axial contact between the resilient sealing member 30 and the seating shoulder 22 of the housing and the radial seating surface 44 of the cap member 40. Thus at least one annular sealing ring 50a and preferably both oppositely orientated annular sealing rings 50a and 50b are compressed to form fluid barriers in the housing.

The orifice 42 of the cap member 40 is preferably sized slightly smaller than the diameter of the bore 18 so that either small cross dimensioned portion 32a or 32b of the resilient sealing member will fit in either the orifice 42 or the bore 18.

Cap member 40 is fixed to housing 12 to achieve the proper axial compression in the resilient sealing member 30. Cap member is fixed to the hosing by thermal or sonic welding or by solvent or adhesive bonding, for example. A friction or snap fit with the housing is also suitable.

Preferably, cavity 20 and bore 18 are circular and the resilient sealing member 30 is a slightly smaller dimensioned circular disk. However, the shapes of the two radial cross dimensions 32 and 34 must merely coincide with the shape of the cavity 20 and the bore 18 so that the sealing member 30 may be easily positioned in the cavity and the bore without any radial interference. Thus, the resilient sealing member would also function acceptably with an oval, square, hexagonal, or any similar symmetric shape. The conformingly shaped resilient sealing member must merely be slightly undersized for cavity 20 and bore 18, so as to fit without interference, that is without radial compression of the resilient sealing member 30.

FIG. 2 shows an exploded view of the components, for example prior to positioning of the undersized resilient sealing member 30 in the conforming, parallel walled cavity 20 of the housing and prior to cap 40 being fixed to the housing 12.

The resilient sealing member 30 in FIG. 1 is subject to equal axial compressive forces of consistent magnitude at all axial points of the contact between the resilient sealing member 30 and housing 12. Further, no radial compressive force are produced. A significant advantage of this distribution of compressive forces is that the sealing member 30 will sufficiently engage and retain an inserted injecting device such as a cannula and resist kickback of the cannula. This reduces the need to depend on an additional retaining mechanism for the cannula.

Figure 4:
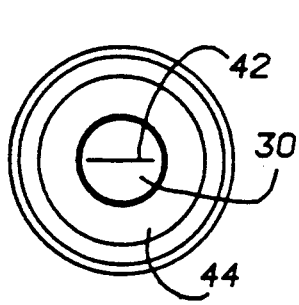
FIG. 4 is top view of FIG. 1.

A preferred embodiment of the sealing member 30 is shown by the pre-pierced resilient sealing member 30 of FIG. 3 and FIG. 4. The resilient sealing member 30 may be pre-pierced with a perforation 42 prior to being positioned in the housing cavity. Alternatively the resilient sealing member 30 may be pre-pierced after it is positioned in the housing cavity. Pre-piercing refers to the axial perforation, such as with a lancing knife, through the resilient sealing member 30. During the assembly process. Pre-piercing occurs prior to the first insertion of an injection or connection device during use. The perforation is normally closed by the resilient character of the member 30.

FIG. 4 is a top view of FIG. 1 and shows the perforation 42 is centered in the sealing member 30 and has a radial dimension that is less than the total cross dimension of the resilient sealing member.

Figure 5:
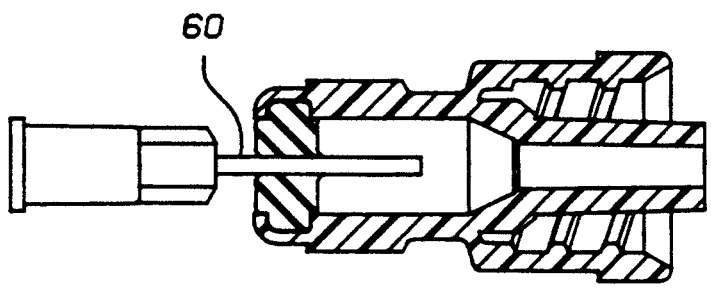
FIG. 5 is a side sectional view of the access site of FIG. 1 having a blunt injection device inserted in the pre-pierced resilient sealing member.

FIG. 5 shows a blunt insertion device 60 such as a blunt steel cannula inserted through the pre-pierced resilient sealing member 30 of the present invention. The axial compression forces tend to engage and retain the inserted cannula in the resilient sealing member 30. There are no pre-existing unbalanced radial compressive forces in the resilient sealing member 30 of the present invention which can act to inadvertently kickback the cannula as compared to other known injection sites previously described.

From the foregoing, it is readily apparent that the access site of the present invention as disclosed herein has many advantages. First, the manufacture and assembly of the device is straightforward since the resilient sealing member 30 does not need special orientation in the housing. Assembling the resilient sealing member into the housing cavity is readily accomplished.

Further, the assembled access site provides several competitive advantages due to the relationship of the diameters of the resilient sealing member and the housing cavity which produces only axial compressive forces along the axial interface between the resilient sealing member and the housing. There are no unbalanced radial compressive forces which would cause the resilient sealing member to walk out of the cavity during assembly. This permits the resilient sealing member to be easily retained in the housing cavity prior to the cap member 40 being installed. Other retaining methods such as a swaged portion of the housing can retain the resilient sealing member as needed.

Furthermore, the equal axial distribution of compressive forces causes the resilient sealing member to sufficiently engage and retain an inserted injection device such as a sharp or blunt cannula. This is in contrast to the kickback forces potentially produced by sealing members having an axial gradient of compressive forces acting on the resilient sealing member.

Another important aspect of the present invention is that the resilient sealing member can be pre-pierced either before the sealing member is positioned in the housing cavity or after the sealing member has been positioned in the housing cavity. Pre-piercing allows a blunt injection device to be used with this type of injection site. The balanced compressive forces of this invention are important to retain the injection device in the pre-pierced resilient sealing member during use and to reseal the sealing member after the injection device is withdrawn.

Although the invention has been described in connection with a male adapter plug, it is readily apparent that the access site may be employed with other types of administration sites such as a Y-site or a injection port on a container or bag.

Although the present invention has been disclosed in terms of a preferred embodiment, it will be apparent to those skilled in the art that variations and modifications can be made without departing from the spirit and scope of the invention as defined in the following claims.

We claim:

1. An access site for a fluid delivery system comprising:
    a rigid tubular housing having an inlet, an outlet and a bore therebetween;
    a cavity at the inlet end of the housing having parallel sidewalls with an internal cross dimension greater than the diameter of the bore;
    a shoulder at the juncture of the cavity and the bore;
    a solid resilient sealing member having a large cross dimensioned portion and a first solid small cross dimensioned portion axially extending from one end of the large dimensioned portion, said first small cross dimensioned portion positioned in the bore of the housing and said large cross dimensioned portion positioned in the inlet cavity of the housing;
    at least one axially protruding annular sealing ring on the large cross dimensioned portion of the resilient sealing member in contact with the shoulder of the housing;
    means for securing said resilient sealing member in said housing such that the resilient sealing member experiences axial compressive forces at all points of axial contact between the resilient sealing member and the housing; and
    an axially parallel perforation through the solid resilient sealing member such that the perforation is normally closed by the resiliency of the resilient sealing member.

2. The access site of claim 1 wherein the perforation is centered in the resilient sealing member and has a radial dimension that is less than the sidewall internal cross dimension.

3. The access site of claim 1 wherein the cavity is cylindrical and the sidewall cross dimension is the diameter of the cylinder.

4. The access site of the claim 3 further including a second small cross dimensioned portion axially extending from an opposite end of the large dimensioned portion of the resilient sealing member.

5. The access site of claim 4 further including a pair of axially opposed annular sealing rings protruding from opposite ends of said large cross dimensioned portion of the resilient sealing member.

6. The access site of claim 5 wherein said securing means further comprises a cap member having a center orifice of the same diameter as the bore of the housing, said cap being fixed to the housing so as to axially compress the seal rings of the resilient sealing member.

* * * * *